United States Patent
Hu et al.

(10) Patent No.: US 11,085,929 B2
(45) Date of Patent: Aug. 10, 2021

(54) NANOSHELL-STRUCTURED MATERIAL AS CO-MATRIX FOR PEPTIDE CHARACTERIZATION IN MASS SPECTROMETRY

(71) Applicants: ARIZONA BOARD OF REGENTS ON BEHALF OF ARIZONA STATE UNIVERSITY, Scottsdale, AZ (US); The Methodist Hospital, Houston, TX (US)

(72) Inventors: Ye Hu, Scottsdale, AZ (US); Yang Bu, Houston, TX (US)

(73) Assignees: ARIZONA BOARD OF REGENTS ON BEHALF OF ARIZONA STATE UNIVERSITY, Scottsdale, AZ (US); THE METHODIST HOSPITAL, Houston, TX (US)

( * ) Notice: Subject to any disclaimer, the term of this patent is extended or adjusted under 35 U.S.C. 154(b) by 0 days.

(21) Appl. No.: 16/119,100

(22) Filed: Aug. 31, 2018

(65) Prior Publication Data
US 2019/0064178 A1    Feb. 28, 2019

Related U.S. Application Data

(60) Provisional application No. 62/553,014, filed on Aug. 31, 2017.

(51) Int. Cl.
| | | |
|---|---|---|
| G01N 33/68 | (2006.01) | |
| C01G 23/053 | (2006.01) | |
| C01G 23/08 | (2006.01) | |

(52) U.S. Cl.
CPC ....... *G01N 33/6851* (2013.01); *C01G 23/053* (2013.01); *C01G 23/08* (2013.01);
(Continued)

(58) Field of Classification Search
CPC ... C01G 23/053; C01G 23/08; C01P 2004/03; C01P 2004/04; C01P 2004/34; C01P 2004/61; G01N 2333/35; G01N 2458/15
See application file for complete search history.

(56) References Cited

U.S. PATENT DOCUMENTS

| | | |
|---|---|---|
| 4,816,567 A | 3/1989 | Cabilly et al. |
| 4,946,778 A | 8/1990 | Ladner et al. |

(Continued)

FOREIGN PATENT DOCUMENTS

| | | |
|---|---|---|
| WO | 1993011161 A1 | 6/1993 |
| WO | 1996002576 A1 | 2/1996 |
| WO | 2018126043 A1 | 7/2018 |

OTHER PUBLICATIONS

Leshuk etal. (ACS Appl. Mater. Interfaces, 2012, vol. 4, pp. 6062-6070, published Oct. 30, 2012). (Year: 2012).*

(Continued)

*Primary Examiner* — Tracy Vivlemore
*Assistant Examiner* — Nam P Nguyen
(74) *Attorney, Agent, or Firm* — Viksnins Harris Padys Malen LLP (57) ABSTRACT

Certain embodiments of the invention provide $TiO_2$ nanoshell particles, methods of fabricating $TiO_2$ nanoshell particles, and methods of enriching peptides in a sample using $TiO_2$ nanoshell particles.

5 Claims, 3 Drawing Sheets
(2 of 3 Drawing Sheet(s) Filed in Color)

(52) U.S. Cl.
CPC ...... *C01P 2004/03* (2013.01); *C01P 2004/04* (2013.01); *C01P 2004/34* (2013.01); *C01P 2004/61* (2013.01); *G01N 2333/35* (2013.01); *G01N 2458/15* (2013.01)

(56) References Cited

U.S. PATENT DOCUMENTS

| | | | |
|---|---|---|---|
| 5,091,513 | A | 2/1992 | Huston et al. |
| 5,260,203 | A | 11/1993 | Ladner et al. |
| 5,455,030 | A | 10/1995 | Ladner et al. |
| 2015/0260715 | A1* | 9/2015 | Hu ............... G01N 33/552 506/12 |
| 2019/0234952 | A1 | 8/2019 | Hu |

OTHER PUBLICATIONS

Guan et al. (Sci. Adv. 2016;2:e1501554, pp. 1-8, published Mar. 4, 2016). (Year: 2016).*
Kim et al. (Chem. Eur. J., 2012, vol. 18, pp. 4902-2908, published Mar. 15, 2012). (Year: 2012).*
Altschul, S, et al., "Basic local alignment search tool", J Mol Biol 215, 403-410 (1990).
Better, et al., "Expression of Engineered Antibodies and Antibody Fragments in Microorganisms", Methods in Enzymology 178, 476-496 (1989).
Bird, et al., "Single Chain Antibody Variable Regions", Tibtech 9, 132-137 (1991).
Brennan, et al., "Preparation of Bispecific Antibodies by Chemical Recombination of Monoclonal Immunoglobulin G1 Fragments", Science 229, 81-83 (1985).
Carter, et al., "High Level *Escherichia coli* Expression and Production of a Bivalent Humanized Antibody Fragment", Bio/Technology 10, 163-167 (1992).
Chen, D, et al., "Mesoporous Anatase TiO2 Beads with High Surface Areas and Controllable Pore Sizes: A Superior Candidate for High-Performance Dye-Sensitized Solar Cells", Adv Mater 21, 2206-2210 (2009).
Clackson, Tim, et al., "Making antibody fragments using phage display libraries", Nature 352, 624-628 (1991).
Co, M, et al., "A humanized antibody specific for the platelet integrin gplll3/llla", J Immunol 152, 2968-2976 (1994).
Dalbadie-McFarland, G., et al., "Oligonucleotide-directed mutagenesis as a general and powerful method for studies of protein function", Proc Natl Acad Sci. 79(21), 6409-6413 (1982).
Holliger, et al., ""Diabodies": Small bivalent and bispecific antibody fragments", Proc. Natl. Acad. Sci. 90, 6444-6448 (1993).
Huston, J, et al., "Protein engineering of antibody binding sites: Recovery of specific activity in an anti-digoxin single-chain Fv analogue produced in *Escherichia coli*", Proc. Natl. Acad. Sci. 85, 5879-5883 (1988).
Jones, et al., "Replacing the complementarity-determining regions in a human antibody with those from a mouse", Nature 321, 522-525 (1986).
Karlin, S, et al., "Applications and statistics for multiple high-scoring segments in molecular sequences", Proc Natl Acad 90, 5873-5877 (1993).
Kohler, et al., "Continuous cultures of fused cells secreting antibody of predefined specificity", Nature 256, 495-497 (1975).
Kunkel, T, "Rapid and efficient site-specific mutagenesis without phenotypic selection", Proc Natl Acad Sci USA 82, 488-492 (1985).
Lamoyi, E, "Preparation of F(ab')2 fragments from mouse IgG of various subclasses", Methods Enzymol 121, 652-663 (1986).
Lu, M, et al., "Nanomaterials as Assisted Matrix of Laser Desorption/Ionization Time-of-Flight Mass Spectrometry for the Analysis of Small Molecules", Nanomaterials 7, 87, 21 pages (2017).
Mark, D, et al., "Site-specific mutagenesis of the human fibroblast interferon gene", Proc Natl Acad Sci. 81(18), 5662-5666 (1984).
Marks, et al., "By-passing immunization. Human antibodies from V-gene libraries displayed on phage", J Mol Biol 222(3), 581-597 (1991).
Marks, et al., "By-Passing Immunization: Building High Affinity Human Antibodies by Chain Shuffling", Bio/ Technology 10, 779-783 (1992).
McCafferty, et al., "Phage antibodies: filamentous phage displaying antibody variable domains", Nature 348, 552-554 (1990).
Morimoto, et al., "Single-step purification of F(ab')2 fragments of mouse monoclonal antibodies (immunoglobulins G1) by hydrophobic interaction high performance liquid chromatography using TSKgel Phenyl-5PW", Journal of Biochemical and Biophysical Methods 24, 107-117 (1992).
Morrison, et al., "Chimeric human antibody molecules: Mouse antigen-binding domains with human constant region domains", Proc. Natl. Acad. Sci. USA 81, 6851-6855 (1984).
NCBI, "Basic Local Alignment Search Tool (BLAST)", U.S. National Library of Medicine, 2 pages (2019).
Pluckthun, "Antibodies from *Escherichia coli*", The Pharmacology of Monoclonal Antibodies, vol. 113, Chapter 11, eds. Rosenburge and Moore, Springer Verlag, N.Y., pp. 269-315 (1994).
Presta, L, "Antibody engineering", Curr. Op. Struct. Biol. vol. 2, 593-596 (1992).
Reichmann, L, et al., "Reshaping human antibodies for therapy", Nature 332(6162), 323-327 (1988).
Rousseaux, J, et al., "Optimal conditions for the preparation of proteolytic fragments from monoclonal IgG of different rat IgG subclasses", Methods Enzymol 121, 663-669 (1986).
Sato, et al., "Reshaping a Human Antibody to Inhibit the Interleukin 6-dependent Tumor Cell Growth", Cancer Res. 53, 851-856 (1993).
Wang, A., et al., "Site-specific mutagenesis of the human interleukin-2 gene: structure-function analysis of the cysteine residues", Science 224(4656), 1431-1433 (1984).
Waterhouse, et al., "Combinatoial infection and in vivo recombination: a strategy for making large phage antibody repertoires", Nucleic Acids Res. 21 (9), 2265-2266 (1993).
Zoller, M, et al., "Oligonucleotide-directed mutagenesis using M13-derived vectors: an efficient and general procedure for the production of point mutations in any fragment of DNA", Nucleic Acids Res. 10(20), 6487-6500 (1982).

* cited by examiner

NANOSHELL-STRUCTURED MATERIAL AS CO-MATRIX FOR PEPTIDE CHARACTERIZATION IN MASS SPECTROMETRY

CROSS-REFERENCE TO RELATED APPLICATION

This patent application claims the benefit of priority of U.S. Application Ser. No. 62/553,014 filed Aug. 31, 2017, which application is herein incorporated by reference.

GOVERNMENT FUNDING

This invention was made with government support under R01 AI122932 awarded by the National Institutes of Health. The government has certain rights in the invention.

BACKGROUND

In the last decade, desorption/ionization mass spectrometry (DIMS) has gained much attention in clinical diagnostic applications because of its high accuracy and high-throughput screening capabilities. However, the use of chemical matrices introduces inherent limitations including the need to select compatible matrices, the interference of chemical matrices in the low-molecular weight range, and poor quality of data (i.e., low sensitivity and poor reproducibility). To overcome these issues, nanostructured materials such as Si nanowires and porous Si substrates were developed to replace chemical matrices. The high-energy laser absorptions on the nanostructured Si materials strongly enhance the efficiency of analyte desorption and ionization. Nevertheless, one common problem in using Si substrates is their high affinity for hydrocarbons and other ambient species. Desorption of these species generates background interference in the low end of the mass spectrum. While analytical techniques suffer some degree of contamination, without a prior chromatographic separation step, this problem could severely limit the application of the technique and/or reduce its sensitivity. A second problem is related to the nature of the ion isolation mechanism. Many biomolecules easily detectable by Electrospray Ionization MS and Nuclear Magnetic Resonance are not amenable to detection by DIMS because the latter method has a strong selectivity toward compounds that have a high-proton affinity, low-ionization energy and high-stabilization energy. A third problem with DIMS is poor quantitative performance due to the poor spot-to-spot precision.

Accordingly, a new platform for enhanced laser desorption/ionization of analytes is needed.

SUMMARY

In certain embodiments, the present invention provides a method of fabricating TiO2 nanoshell particles comprising: (a) dissolving 1-Hexadecylamine in alcohol, (b) adding polymer beads to form a precursor solution, (c) adding an ammonia solution to the precursor solution, (d) adding Titanium butoxide (TBT) to form $PS/TiO_2$ amorphous beads, (e) washing the PS/TiO2 amorphous beads with ethanol to remove the free hydrolyzed $TiO_2$ to form a white suspension.

In certain embodiments, the present invention provides Nanoshell particles comprising anatase $TiO_2$ Mesoporous Hollow Nano Spheres (MHNSs) prepared by the method described above.

In certain embodiments, the present invention provides Nanoshell particles comprising anatase $TiO_2$ Mesoporous Hollow Nano Spheres (MHNSs) of about 0.5 μm to 1.2 μm in diameter and having a shell thickness of about 20 nm to 200 nm.

In certain embodiments, the present invention provides a material for peptide characterization in mass spectrometry comprising a plurality of binding agents operably linked to a nanoshell, wherein the nanoshell comprises anatase $TiO_2$ MHNS of about 0.5 μm to 1.2 μm in diameter and having a shell thickness of about 20 nm to 200 nm.

In certain embodiments, the present invention provides a method of enriching peptides in a sample comprising contacting the material described above with a sample, and processing the sample by mass spectrometry (MS).

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 provides a conceptual drawing of an embodiment of a process of the present invention. Schematic depicting affinity-based NanoShell-MS. (Top left) TB patient serum is digested for 5 minutes then supplemented with internal standards, and then (Top right) mixed with antibody-conjugated NanoShells. (Bottom left) Mtb antigen-derived peptides are bound to the NanoShells and (Bottom right) laser ionization of bound Mtb peptides for MALDI-TOF MS quantitation against internal standards.

FIGS. 2A-2F. FIGS. 2A and 2B provide SEM images of PS-TiO2 core-shell nano spheres; FIGS. 2C and 2D provide SEM images of TiO2 mesoporous hollow nanospheres (MHNSs); FIGS. 2E and 2F provide TEM images of TiO2 mesoporous hollow nanospheres; SEM, scanning electron microscopy; TEM, transmission electron microscopy.

FIGS. 3A-3D provide MALDI-TOF Spectra of standard CFP-10 tryptic digested peptides in water, concentrations. FIG. 3A: 800 nM; FIG. 3B: 40 nM; FIG. 3C: 2 nM.

DETAILED DESCRIPTION

Figure 1:
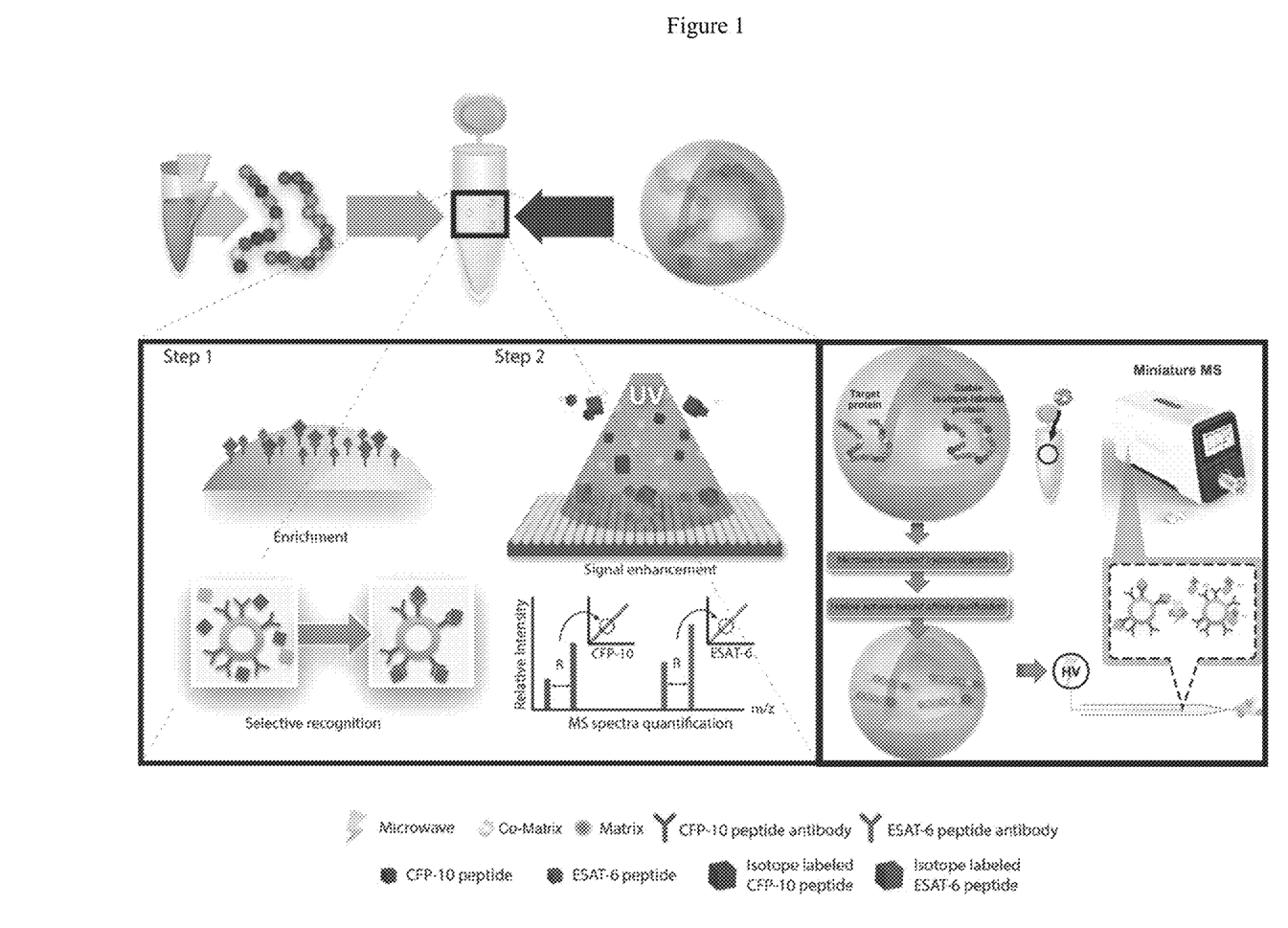
Figures 2A, 2F:
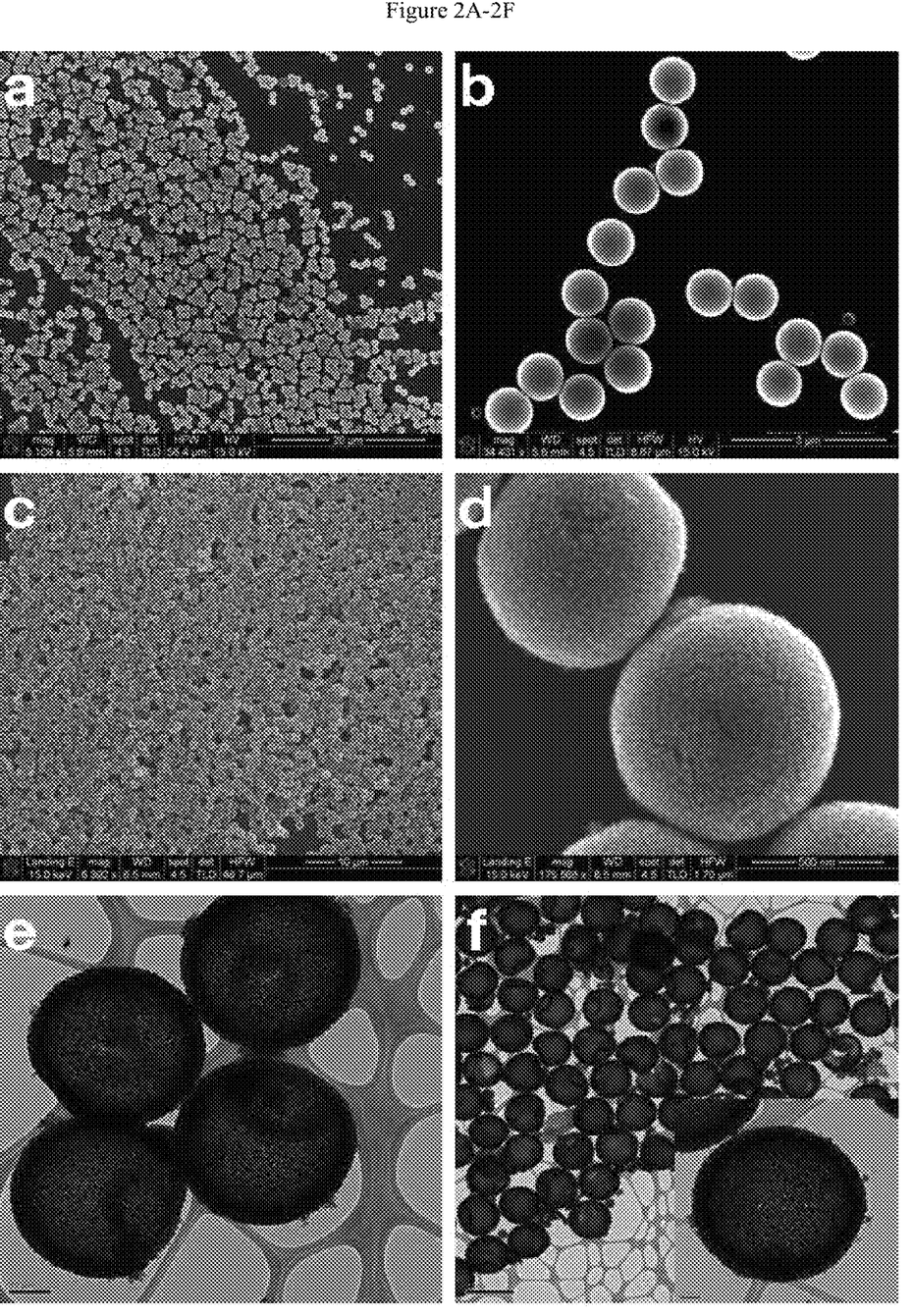
Figure 3A:
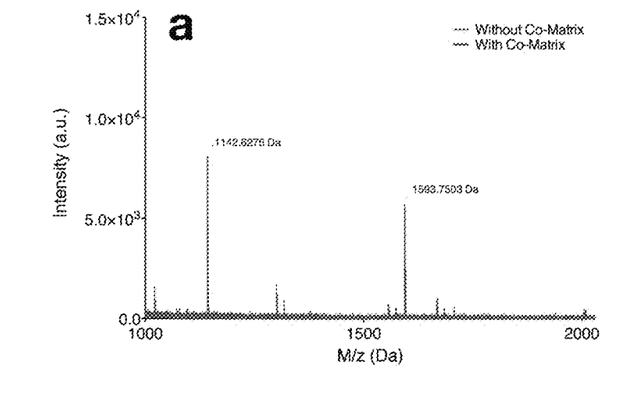
Figure 3B:
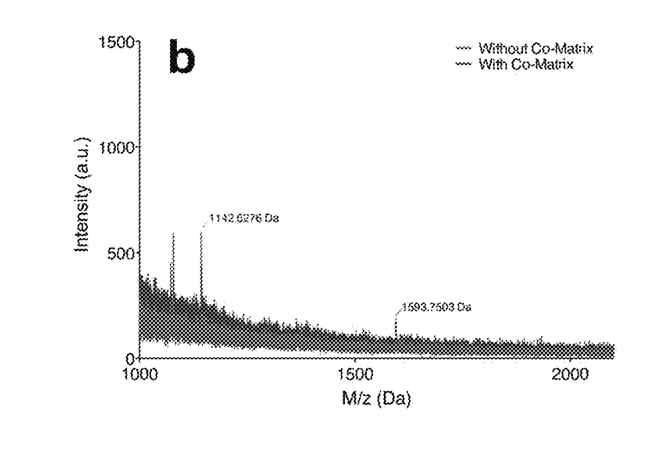
Figure 3C:
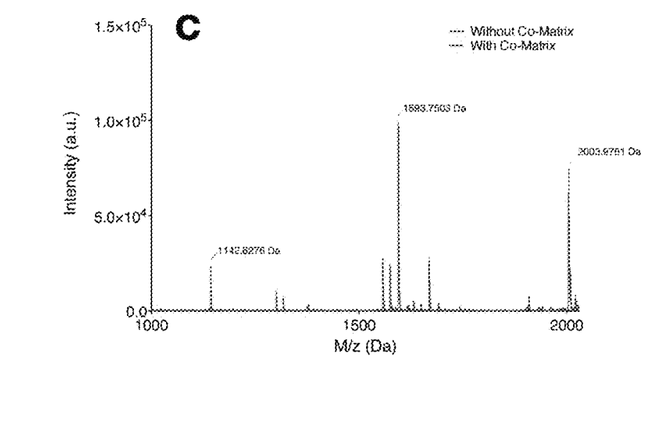
Figure 3D:
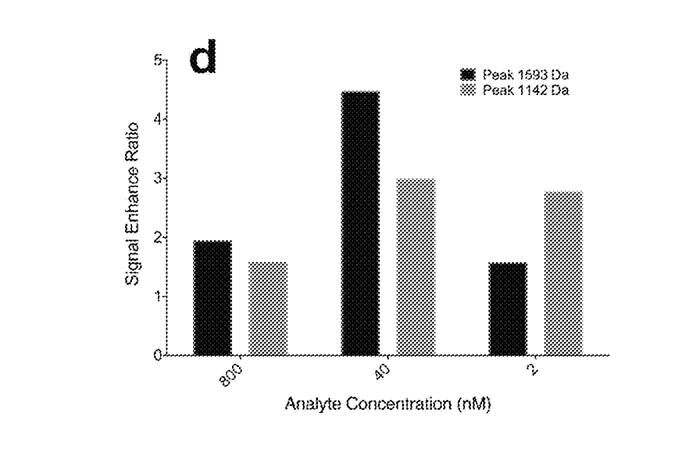
FIG. 3D Signal Enhance ratios for different concentrations of CFP-10 with $TiO_2$ mesoporous hollow nanospheres as the co-matrix material.

To address the obstacles posed by current desorption/ionization mass spectrometry (DIMS) methods for detecting low-abundance biomarkers, a new platform comprised of a TiO2 nanoshell for enhanced laser desorption/ionization of analytes was developed. By controlling the size, surface density, and the shell thickness of $TiO_2$ particle, it is possible to set the optical and surface properties of $TiO_2$ particle and to generate appropriate particles as a co-matrix for very sensitive detection of target peptides. Uniform coverage of peptide antibodies on the nanoshell surface can help to eliminate nonspecific binding of species in biological fluids and enhances the MS signals. To demonstrate proof-of-principle, polyclonal anti-CFP-10 and anti-ESAT-6 antibodies were conjugated on a nanoshell. After extensive washing to remove unbound molecules, nanoshells loaded with bound target peptides were processed on MS, where ionization by UV laser facilitated detection at very low concentrations (sub-fetomolar).

Detection of small, low abundance proteins or peptides in human bodily fluid is very challenging due to the large dynamic range of proteins in such complex mixtures. $TiO_2$ NanoShells have been generated that have energy absorption across the spectrum of the UV laser employed in MALDI-TOF MS as a co-matrix to enhance analyte desorption/ionization, and thus detection sensitivity. With the addition of peptide antibody-conjugated NanoShell particles, the high sensitivity and specificity in the selective enrichment of *Mycobacterium* antigen peptides has been shown.

The present NanoShells offer high surface area for laser absorption, efficiently transfer energy to maximize peptide detection, and can be optimized to detect targets at a 0.1 fmol limit. The nanoshells allow for selectively enriching a large variety of serum protein/peptide markers and preserve them "in-NanoShell" for long-term storage and subsequent MS analysis, providing opportunities to investigate other clinically relevant indications.

The present $TiO_2$ NanoShells are constructed from a robust inorganic material, and can be manufactured in large quantities at very low cost (~$3 per test), rendering them suitable for use in resource-limited settings.

Applying nanotechnology to the biosciences offers an enormous advantage due to immediate access to an array of sophisticated tools. Scalability, precision, and reproducibility are valuable characteristics of the NanoShell micromachining processes that can be translated into clinical applications.

The NanoShell-MS significantly reduces, if not eliminates, nonspecific recognition seen with immunoassays and thus diminishes the rate of clinical false-positives, a top priority in infectious disease diagnosis.

Fabrication of $TiO_2$ NanoShell Particles

The $TiO_2$ Mesoporous Hollow Nano spheres (MHNSs) were prepared by modifying a previous report (D. Chen, F. Huang, Y.-B. Cheng and R. A. Caruso, *Adv. Mater.*, 2009, 21, 2206-2210) using a sol-gel, hydrothermal and calcination three-step process. Briefly, 1-Hexadecylamine (30 mg) was dissolved in 100 mL ethanol under magnetic stirring, followed by the addition of 20 μL PS Latex beads (mean particles size: 0.8 μm) to form a precursor solution. Afterwards, to the precursor solution, 500 μL ammonia solution (28%-30%) were added and stir for 15 minutes before adding 500 μL Titanium butoxide (TBT) drop-wisely under stirring at 1200 rpm and react for exact 90 minutes, the obtained white suspension was washed with ethanol at 2000 rpm for 10 minutes three times to remove the free hydrolyzed TiO2 and then get dried in vacuum. A further hydrothermal process was adapted to form a highly crystalline framework. The prepared $PS/TiO_2$ amorphous beads were re-dispersed in 12 mL ethanol and 6 mL deionized water, sealed within a Teflon-lined autoclave (30 mL) and heated at 180° C. for 8 h. The obtained $PS/TiO_2$ were washed and dried at 50° C. in vacuum, followed by calcination at 500° C. for 5 hours to remove the PS template and obtain the anatase $TiO_2$ MHNSs.

In certain embodiments, the present invention provides a method of fabricating $TiO_2$ nanoshell particles comprising: (a) dissolving 1-Hexadecylamine in alcohol, (b) adding polymer beads to form a precursor solution, (c) adding an ammonia solution to the precursor solution, (d) adding Titanium butoxide (TBT) to form PS/TiO2 amorphous beads, (e) washing the PS/TiO2 amorphous beads with ethanol to remove the free hydrolyzed TiO2.

In certain embodiments, the alcohol is ethanol.

In certain embodiments, the polymer beads are polystyrene (PS) Latex, Silica or Silicon beads.

In certain embodiments, the polymer beads have a mean particle size of about 0.5-1.2 μm.

In certain embodiments, the ammonia solution is at a concentration of 20%-40% v/v.

In certain embodiments, the ammonia solution is at a concentration of 28%-30% v/v.

In certain embodiments, the stirring in step (c) is for about 10-20 minutes.

In certain embodiments, the stirring in step (c) is for about 15 minutes.

In certain embodiments, the white suspension in step (e) is washed two or three times.

In certain embodiments, the method further comprises (f) drying in a vacuum.

In certain embodiments, the method further comprises: (g) dispersing the $PS/TiO_2$ amorphous beads in an ethanol solution, sealed within a Teflon-lined autoclave and heated at about 175° C. to 185° C. for about 7.5 to 8.5 hours to form a highly crystalline $PS/TiO_2$ framework, (h) washing the highly crystalline $PS/TiO_2$ framework, drying the highly crystalline $PS/TiO_2$ framework at a temperature suitable for drying in vacuum, and (i) calcinating at 450° C. to 550° C. for 4.5 to 5.5 hours to remove the PS template and obtain anatase $TiO_2$ Mesoporous Hollow Nano Spheres (MHNSs).

In certain embodiments, in step (g) the beads are heated at about 180° C. for about 8 hours.

In certain embodiments, in step (g) the ethanol solution is 2:1 ethanol:deionized water (v/v).

In certain embodiments, in step (h) the temperature is at about 50° C.

In certain embodiments, in step (i) the calcinating is at a temperature of about 500° C. for about 5 hours.

In certain embodiments, the present invention provides Nanoshell particles comprising anatase $TiO_2$ Mesoporous Hollow Nano Spheres (MHNSs) prepared by the method described above.

In certain embodiments, the present invention provides Nanoshell particles comprising anatase $TiO_2$ Mesoporous Hollow Nano Spheres (MHNSs) of about 0.5 μm to 1.2 μm in diameter and having a shell thickness of about 20 nm to 200 nm.

In certain embodiments, the present invention provides a material for peptide characterization in mass spectrometry comprising a plurality of binding agents operably linked to a nanoshell, wherein the nanoshell comprises anatase $TiO_2$ MHNS of about 0.5 μm to 1.2 μm in diameter and having a shell thickness of about 20 nm to 200 nm.

In certain embodiments, the plurality of binding agents are antibodies or antibody fragments.

In certain embodiments, the antibodies are selective for *Mycobacterium* antigen peptides.

In certain embodiments, the antibodies are polyclonal anti-CFP-10 or anti-ESAT-6 antibodies.

In certain embodiments, the present invention provides a method of enriching peptides in a sample comprising contacting the material of described above with a sample, and processing the sample by mass spectrometry (MS).

In certain embodiments, the sample is a biological fluid sample.

In certain embodiments, the MS is matrix-assisted laser desorption/ionization Time of Flight MALDI-TOF MS.

Binding Agents

The present invention provides a purified binding agent (or ligand) that binds specifically to a target protein (e.g., an antigen). The binding agent can be an antibody or a small molecule agent. Examples of binding agents include monoclonal or polyclonal antibodies, peptides, small molecules, small interfering RNAs, etc. In certain embodiments, the binding agent is an antibody or antibody fragment. In certain embodiments, the antibody is selective for *Mycobacterium* antigen peptides. In certain embodiments, the antibodies are polyclonal anti-CFP-10 or anti-ESAT-6 antibodies.

Antibodies

As used herein, the term "antibody" includes scFv, humanized, fully human or chimeric antibodies, single-chain antibodies, diabodies, and antigen-binding fragments of antibodies that do not contain the Fc region (e.g., Fab fragments). In certain embodiments, the antibody is a human antibody or a humanized antibody. A "humanized" antibody contains only the three CDRs (complementarity determining regions) and sometimes a few carefully selected "framework" residues (the non-CDR portions of the variable regions) from each donor antibody variable region recombinantly linked onto the corresponding frameworks and constant regions of a human antibody sequence. A "fully humanized antibody" is created in a hybridoma from mice genetically engineered to have only human-derived antibody genes or by selection from a phage-display library of human-derived antibody genes.

As used herein, the term "antibody" includes a single-chain variable fragment (scFv or "nanobody"), humanized, fully human or chimeric antibodies, single-chain antibodies, diabodies, and antigen-binding fragments of antibodies (e.g., Fab fragments). A scFv is a fusion protein of the variable region of the heavy ($V_H$) and light chains ($V_L$) of an immunoglobulin that is connected by means of a linker peptide. The linker is usually short, about 10-25 amino acids in length. If flexibility is important, the linker will contain a significant number of glycines. If solubility is important, serines or theonines will be utilized in the linker. The linker may link the amino-terminus of the $V_H$ to the carboxy-terminus of the $V_L$, or the linker may link the carboxy-terminus of the $V_H$ to the amino-terminus of the $V_L$. Divalent (also called bivalent) scFvs can be generated by linking two scFvs. For example, a divalent scFv can be made by generating a single peptide containing two $V_H$ and two $V_L$ regions. Alternatively, two peptides, each containing a single $V_H$ and a single $V_L$ region can be dimerized (also called "diabodies"). Holliger et al., "Diabodies: small bivalent and bispecific antibody fragments," PNAS, July 1993, 90:6444-6448. Bivalency allows antibodies to bind to multimeric antigens with high avidity, and bispecificity allows the cross-linking of two antigens.

As used herein, the term "monoclonal antibody" refers to an antibody obtained from a group of substantially homogeneous antibodies, that is, an antibody group wherein the antibodies constituting the group are homogeneous except for naturally occurring mutants that exist in a small amount. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against diverse antigenic determinants. In addition to their specificity, monoclonal antibodies are advantageous in that they are produced from hybridoma cultures not contaminated with other immunoglobulins.

The adjective "monoclonal" indicates a characteristic of antibodies obtained from a substantially homogeneous group of antibodies, and does not specify antibodies produced by a particular method. For example, a monoclonal antibody to be used in the present invention can be produced by, for example, hybridoma methods (Kohler and Milstein, Nature 256:495, 1975) or recombination methods (U.S. Pat. No. 4,816,567). The monoclonal antibodies used in the present invention can be also isolated from a phage antibody library (Clackson et al., Nature 352:624-628, 1991; Marks et al., J. Mol. Biol. 222:581-597, 1991). The monoclonal antibodies of the present invention particularly comprise "chimeric" antibodies (immunoglobulins), wherein a part of a heavy (H) chain and/or light (L) chain is derived from a specific species or a specific antibody class or subclass, and the remaining portion of the chain is derived from another species, or another antibody class or subclass. Furthermore, mutant antibodies and antibody fragments thereof are also comprised in the present invention (U.S. Pat. No. 4,816,567; Morrison et al., Proc. Natl. Acad. Sci. USA 81:6851-6855, 1984).

As used herein, the term "mutant antibody" refers to an antibody comprising a variant amino acid sequence in which one or more amino acid residues have been altered. For example, the variable region of an antibody can be modified to improve its biological properties, such as antigen binding. Such modifications can be achieved by site-directed mutagenesis (see Kunkel, Proc. Natl. Acad. Sci. USA 82: 488 (1985)), PCR-based mutagenesis, cassette mutagenesis, and the like. Such mutants comprise an amino acid sequence which is at least 70% identical to the amino acid sequence of a heavy or light chain variable region of the antibody, more preferably at least 75%, even more preferably at least 80%, still more preferably at least 85%, yet more preferably at least 90%, and most preferably at least 95% identical. As used herein, the term "sequence identity" is defined as the percentage of residues identical to those in the antibody's original amino acid sequence, determined after the sequences are aligned and gaps are appropriately introduced to maximize the sequence identity as necessary.

Specifically, the identity of one nucleotide sequence or amino acid sequence to another can be determined using the algorithm BLAST, by Karlin and Altschul (Proc. Natl. Acad. Sci. USA, 90: 5873-5877, 1993). Programs such as BLASTN and BLASTX were developed based on this algorithm (Altschul et al., J. Mol. Biol. 215: 403-410, 1990). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); http://www.ncbi.nlm.nih.gov).

Polyclonal and monoclonal antibodies can be prepared by methods known to those skilled in the art.

In another embodiment, antibodies or antibody fragments can be isolated from an antibody phage library, produced by using the technique reported by McCafferty et al. (Nature 348:552-554 (1990)). Clackson et al. (Nature 352:624-628 (1991)) and Marks et al. (J. Mol. Biol. 222:581-597 (1991)) reported on the respective isolation of mouse and human antibodies from phage libraries. There are also reports that describe the production of high affinity (nM range) human antibodies based on chain shuffling (Marks et al., Bio/Technology 10:779-783 (1992)), and combinatorial infection and in vivo recombination, which are methods for constructing large-scale phage libraries (Waterhouse et al., Nucleic Acids Res. 21:2265-2266 (1993)). These technologies can also be used to isolate monoclonal antibodies, instead of using conventional hybridoma technology for monoclonal antibody production.

Antibodies to be used in the present invention can be purified by a method appropriately selected from known methods, such as the protein A-Sepharose method, hydroxyapatite chromatography, salting-out method with sulfate, ion exchange chromatography, and affinity chromatography, or by the combined use of the same.

The present invention may use recombinant antibodies, produced by gene engineering. The genes encoding the antibodies obtained by a method described above are isolated from the hybridomas. The genes are inserted into an appropriate vector, and then introduced into a host (see, e.g., Carl, A. K. Borrebaeck, James, W. Larrick, Therapeutic Monoclonal Antibodies, Published in the United Kingdom by Macmillan Publishers Ltd, 1990). The present invention provides the nucleic acids encoding the antibodies of the present invention, and vectors comprising these nucleic acids. Specifically, using a reverse transcriptase, cDNAs encoding the variable regions (V regions) of the antibodies are synthesized from the mRNAs of hybridomas. After obtaining the DNAs encoding the variable regions of antibodies of interest, they are ligated with DNAs encoding desired constant regions (C regions) of the antibodies, and the resulting DNA constructs are inserted into expression vectors. Alternatively, the DNAs encoding the variable regions of the antibodies may be inserted into expression vectors comprising the DNAs of the antibody C regions. These are inserted into expression vectors so that the genes are expressed under the regulation of an expression regulatory region, for example, an enhancer and promoter. Then, host cells are transformed with the expression vectors to express the antibodies. The present invention provides cells expressing antibodies of the present invention. The cells expressing antibodies of the present invention include cells and hybridomas transformed with a gene of such an antibody.

The antibodies of the present invention also include antibodies that comprise complementarity-determining regions (CDRs), or regions functionally equivalent to CDRs. The term "functionally equivalent" refers to comprising amino acid sequences similar to the amino acid sequences of CDRs of any of the monoclonal antibodies isolated in the Examples. The term "CDR" refers to a region in an antibody variable region (also called "V region"), and determines the specificity of antigen binding. The H chain and L chain each have three CDRs, designated from the N terminus as CDR1, CDR2, and CDR3. There are four regions flanking these CDRs: these regions are referred to as "framework," and their amino acid sequences are highly conserved. The CDRs can be transplanted into other antibodies, and thus a recombinant antibody can be prepared by combining CDRs with the framework of a desired antibody. One or more amino acids of a CDR can be modified without losing the ability to bind to its antigen. For example, one or more amino acids in a CDR can be substituted, deleted, and/or added.

In certain embodiments, an amino acid residue is mutated into one that allows the properties of the amino acid side-chain to be conserved. Examples of the properties of amino acid side chains comprise: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chains (R, K, H); and aromatic-containing side-chains (H, F, Y, W). The letters within parenthesis indicate the one-letter amino acid codes. Amino acid substitutions within each group are called conservative substitutions. It is well known that a polypeptide comprising a modified amino acid sequence in which one or more amino acid residues is deleted, added, and/or substituted can retain the original biological activity (Mark D. F. et al., Proc. Natl. Acad. Sci. U.S.A. 81:5662-5666 (1984); Zoller M. J. and Smith M., Nucleic Acids Res. 10: 6487-6500 (1982); Wang A. et al., Science 224: 1431-1433; Dalbadie-McFarland G. et al., Proc. Natl. Acad. Sci. U.S.A. 79: 6409-6413 (1982)). The number of mutated amino acids is not limited, but in general, the number falls within 40% of amino acids of each CDR, and preferably within 35%, and still more preferably within 30% (e.g., within 25%). The identity of amino acid sequences can be determined as described herein.

In the present invention, recombinant antibodies artificially modified to reduce heterologous antigenicity against humans can be used. Examples include chimeric antibodies and humanized antibodies. These modified antibodies can be produced using known methods. A chimeric antibody includes an antibody comprising variable and constant regions of species that are different to each other, for example, an antibody comprising the antibody heavy chain and light chain variable regions of a nonhuman mammal such as a mouse, and the antibody heavy chain and light chain constant regions of a human. Such an antibody can be obtained by (1) ligating a DNA encoding a variable region of a mouse antibody to a DNA encoding a constant region of a human antibody; (2) incorporating this into an expression vector; and (3) introducing the vector into a host for production of the antibody.

A humanized antibody, which is also called a reshaped human antibody, is obtained by substituting an H or L chain complementarity determining region (CDR) of an antibody of a nonhuman mammal such as a mouse, with the CDR of a human antibody. Conventional genetic recombination techniques for the preparation of such antibodies are known (see, for example, Jones et al., Nature 321: 522-525 (1986); Reichmann et al., Nature 332: 323-329 (1988); Presta Curr. Op. Struct. Biol. 2: 593-596 (1992)). Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see, European Patent Application No. EP 239,400, and International Patent Application No. WO 96/02576). Human antibody FRs that are ligated via the CDR are selected where the CDR forms a favorable antigen-binding site. The humanized antibody may comprise additional amino acid residue(s) that are not included in the CDRs introduced into the recipient antibody, nor in the framework sequences. Such amino acid residues are usually introduced to more accurately optimize the antibody's ability to recognize and bind to an antigen. For example, as necessary, amino acids in the framework region of an antibody variable region may be substituted such that the CDR of a reshaped human antibody forms an appropriate antigen-binding site (Sato, K. et al., Cancer Res. (1993) 53, 851-856).

The isotypes of the antibodies of the present invention are not limited. The isotypes include, for example, IgG (IgG1, IgG2, IgG3, and IgG4), IgM, IgA (IgA1 and IgA2), IgD, and IgE. The antibodies of the present invention may also be antibody fragments comprising a portion responsible for antigen binding, or a modified fragment thereof. The term "antibody fragment" refers to a portion of a full-length antibody, and generally to a fragment comprising an antigen-binding domain or a variable region. Such antibody fragments include, for example, Fab, F(ab')$_2$, Fv, single-chain Fv (scFv) which comprises a heavy chain Fv and a light chain Fv coupled together with an appropriate linker, diabody (diabodies), linear antibodies, and multispecific antibodies prepared from antibody fragments. Previously, antibody fragments were produced by digesting natural antibodies with a protease; currently, methods for expressing them as recombinant antibodies using genetic engineering techniques are also known (see Morimoto et al., Journal of Biochemical and Biophysical Methods 24:107-117 (1992); Brennan et al., Science 229:81 (1985); Co, M. S. et al., J. Immunol., 1994, 152, 2968-2976; Better, M. & Horwitz, A. H., Methods in Enzymology, 1989, 178, 476-496, Academic Press, Inc.; Plueckthun, A. & Skerra, A., Methods in Enzymology, 1989, 178, 476-496, Academic Press, Inc.; Lamoyi, E., Methods in Enzymology, 1989, 121, 663-669; Bird, R. E. et al., TIBTECH, 1991, 9, 132-137).

An "Fv" fragment is the smallest antibody fragment, and contains a complete antigen recognition site and a binding site. This region is a dimer ($V_H$-$V_L$ dimer) wherein the variable regions of each of the heavy chain and light chain are strongly connected by a noncovalent bond. The three CDRs of each of the variable regions interact with each other to form an antigen-binding site on the surface of the $V_H$-$V_L$ dimer. In other words, a total of six CDRs from the heavy and light chains function together as an antibody's antigen-binding site. However, a variable region (or a half Fv, which contains only three antigen-specific CDRS) alone is also known to be able to recognize and bind to an antigen, although its affinity is lower than the affinity of the entire binding site. Thus, a preferred antibody fragment of the present invention is an Fv fragment, but is not limited thereto. Such an antibody fragment may be a polypeptide that comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody. A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody," even when it is not identical to an antibody fragment produced by protease digestion. Fab'-SH is Fab' with one or more cysteine residues having free thiol groups in its constant region. A F(ab') fragment is produced by cleaving the disulfide bond between the cysteine residues in the hinge region of F(ab')$_2$. Other chemically crosslinked antibody fragments are also known to those skilled in the art. Pepsin digestion of an antibody yields two fragments; one is a F(ab')2 fragment which comprises two antigen-binding domains and can cross-react with antigens, and the other is the remaining fragment (referred to as pFc'). Herein, an antibody fragment equivalent to that obtained by pepsin digestion is referred to as a "F(ab')$_2$-like antibody" when it comprises two antigen-binding domains and can cross-react with antigens. Such antibody fragments can also be produced, for example, by genetic engineering. Such antibody fragments can also be isolated, for example, from the antibody phage library described above. Alternatively, F(ab')$_2$-SH fragments can be recovered directly from hosts, such as E. coli, and then allowed to form F(ab')$_2$ fragments by chemical crosslinking (Carter et al., Bio/Technology 10:163-167 (1992)). In an alternative method, F(ab')2 fragments can be isolated directly from a culture of recombinant hosts.

The term "diabody (Db)" refers to a bivalent antibody fragment constructed by gene fusion (for example, P. Holliger et al., Proc. Natl. Acad. Sci. USA 90: 6444-6448 (1993), EP 404,097, WO 93/11161). In general, a diabody is a dimer of two polypeptide chains. In the each of the polypeptide chains, a light chain variable region ($V_L$) and a heavy chain variable region ($V_H$) in an identical chain are connected via a short linker, for example, a linker of about five residues, so that they cannot bind together. Because the linker between the two is too short, the $V_L$ and $V_H$ in the same polypeptide chain cannot form a single chain V region fragment, but instead form a dimer. Thus, a diabody has two antigen-binding domains. When the $V_L$ and $V_H$ regions against the two types of antigens (a and b) are combined to form $V_{La}$-$V_{Hb}$ and $V_{Lb}$-$V_{Ha}$ via a linker of about five residues, and then co-expressed, they are secreted as bispecific Dbs. The antibodies of the present invention may be such Dbs.

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, N.Y., pp. 269-315 (1994)). Methods for preparing single-chain antibodies are known in the art (see, for example, U.S. Pat. Nos. 4,946,778; 5,260,203; 5,091,513; and 5,455,030). In such scFvs, the heavy chain V region and the light chain V region are linked together via a linker, preferably, a polypeptide linker (Huston, J. S. et al., Proc. Natl. Acad. Sci. U.S.A, 1988, 85, 5879-5883). The heavy chain V region and the light chain V region in a scFv may be derived from the same antibody, or from different antibodies. The peptide linker used to ligate the V regions may be any single-chain peptide consisting of 12 to 19 residues. A DNA encoding a scFv can be amplified by PCR using, as a template, either the entire DNA, or a partial DNA encoding a desired amino acid sequence, selected from a DNA encoding the heavy chain or the V region of the heavy chain of the above antibody, and a DNA encoding the light chain or the V region of the light chain of the above antibody; and using a primer pair that defines the two ends. Further amplification can be subsequently conducted using a combination of the DNA encoding the peptide linker portion, and the primer pair that defines both ends of the DNA to be ligated to the heavy and light chain respectively. After constructing DNAs encoding scFvs, conventional methods can be used to obtain expression vectors comprising these DNAs, and hosts transformed by these expression vectors. Furthermore, scFvs can be obtained according to conventional methods using the resulting hosts. These antibody fragments can be produced in hosts by obtaining genes that encode the antibody fragments and expressing these as outlined above. Antibodies bound to various types of molecules, such as polyethylene glycols (PEGs), may be used as modified antibodies. Methods for modifying antibodies are already established in the art. The term "antibody" in the present invention also encompasses the above-described antibodies.

The antibodies obtained can be purified to homogeneity. The antibodies can be isolated and purified by a method routinely used to isolate and purify proteins. The antibodies can be isolated and purified by the combined use of one or more methods appropriately selected from column chromatography, filtration, ultrafiltration, salting out, dialysis, preparative polyacrylamide gel electrophoresis, and isoelectrofocusing, for example (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory, 1988). Such methods are not limited to those listed above. Chromatographic methods include affinity chromatography, ion exchange chromatography, hydrophobic chromatography, gel filtration, reverse-phase chromatography, and adsorption chromatography. These chromatographic methods can be practiced using liquid phase chromatography, such as HPLC and FPLC. Columns to be used in affinity chromatography include protein A columns and protein G columns. For example, protein A columns include Hyper D, POROS, and Sepharose F. F. (Pharmacia). Antibodies can also be purified by utilizing antigen binding, using carriers on which antigens have been immobilized.

The antibodies of the present invention can be formulated according to standard methods (see, for example, Remington's Pharmaceutical Science, latest edition, Mark Publishing Company, Easton, U.S.A), and may comprise pharmaceutically acceptable carriers and/or additives. The present invention relates to compositions (including reagents and pharmaceuticals) comprising the antibodies of the invention, and pharmaceutically acceptable carriers and/or additives. Exemplary carriers include surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethyl cellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The composition may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, it can comprise an isotonic solution comprising, for example, physiological saline, dextrose, and other adjuvants, including, for example, D-sorbitol, D-mannose, D-mannitol, and sodium chloride, which can also contain an appropriate solubilizing agent, for example, alcohol (for example, ethanol), polyalcohol (for example, propylene glycol and PEG), and non-ionic detergent (polysorbate 80 and HCO-50).

The invention will now be illustrated by the following non-limiting Examples.

Example 1

The matrix solution was prepared by fully dissolving 4 g/L of a-cyano-4-hydroxycinnamic acid (CHCA) in 50% ACN and 0.1% TFA (v/v). The H-mTiO$_2$ co-matrix solution was treated by sonication prior to use. 1 µL analyte solution was spotted on the target plate after mixing with 1 µL co-matrix solution (or without as the control) and allowed to dry completely in vacuum. Following, 1 µL matrix solution was pipetted on the dried analyte H-MTiO$_2$ mixture and allowed to dry before taken to MS analysis. MALDI-TOF MS experiments were performed in the positive ion mode using a Microflex mass spectrometer (Bruker Daltonics, Bremen, Germany). A pulsed nitrogen laser (337 nm) was facilitate in the system, which was operated under high vacuum below $10^{-6}$ Torr, under reflection mode. The ion source voltages, lens voltage, reflector voltage, were 19 kV, 16.75 kV, 9.6 kV, 20.0 kV respectively, and with a delay time of 100 ns, without cutoff mass. The mass spectrum for each sample was collected from 1000 laser shots under a laser intensity of 55%, and calibrated by a peptide calibration standard externally. The raw data of each mass spectrum was acquired and analyzed with flexAnalysis 3.0 software (Bruker Daltonics).

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A material for peptide characterization in mass spectrometry comprising a plurality of binding agents directly conjugated to a nanoshell, wherein the nanoshell consists of anatase $TiO_2$ Mesoporous Hollow Nano Sphere (MHNS) of about 0.5 μm to 1.2 μm in diameter and having a shell thickness of about 20 nm to 200 nm, wherein the plurality of binding agents are antibodies or antibody fragments.

2. The material of claim 1, wherein the antibodies are specific for *Mycobacterium* antigen peptides.

3. The material of claim 1, wherein the antibodies are polyclonal anti-CFP-10 or anti-ESAT-6 antibodies.

4. A method of enriching peptides in a sample comprising contacting the material of claim 1 with a sample and processing the sample by mass spectrometry (MS).

5. The method of claim 4, wherein the MS is matrix-assisted laser desorption/ionization Time of Flight MALDI-TOF MS.

* * * * *